(12) United States Patent
Chen et al.

(10) Patent No.: US 9,297,724 B2
(45) Date of Patent: Mar. 29, 2016

(54) SAMPLE COLLECTION AND TRANSPORT DEVICES, METHODS, AND KITS

(71) Applicant: Sekisui Diagnostics, LLC, Framingham, MA (US)

(72) Inventors: Fon-Chiu Mia Chen, Ramona, CA (US); Melanie Fadul, Walnut, CA (US); Hong Law, San Diego, CA (US); Edward Lee, La Jolla, CA (US); Ann Marie Nanale, San Diego, CA (US); Jeffery White, San Diego, CA (US)

(73) Assignee: Sekisui Diagnostics LLC, Lexington, MA (US)

( * ) Notice: Subject to any disclaimer, the term of this patent is extended or adjusted under 35 U.S.C. 154(b) by 308 days.

(21) Appl. No.: 13/762,228

(22) Filed: Feb. 7, 2013

(65) Prior Publication Data

US 2013/0247694 A1   Sep. 26, 2013

Related U.S. Application Data

(60) Provisional application No. 61/597,676, filed on Feb. 10, 2012.

(51) Int. Cl.
*B01L 99/00* (2010.01)
*G01N 1/10* (2006.01)
*B01L 3/00* (2006.01)

(52) U.S. Cl.
CPC ............... *G01N 1/10* (2013.01); *B01L 3/5055* (2013.01); *B01L 2200/141* (2013.01);
(Continued)

(58) Field of Classification Search
CPC ... G01N 1/00; G01N 1/405; G01N 2001/005; G01N 2001/1037; G01N 2001/007; G01N 2035/00108; B01L 2300/0825; B01L 3/5023; B01L 2300/046

USPC ............... 73/863–865; 600/562–54; 422/409, 422/419, 430, 560–561, 942, 844; 435/287.3, 287.6–287.9, 288.3–288.4

See application file for complete search history.

(56) References Cited

U.S. PATENT DOCUMENTS 3,849,256 A * 11/1974 Linder ........................ 435/287.7
5,215,713 A 6/1993 Steinbiss ........................ 422/61
(Continued)

FOREIGN PATENT DOCUMENTS

DE   199 09 166        7/2000
EP   0467175 A2        7/1991
(Continued)

OTHER PUBLICATIONS

International Bureau of WIPO, Authorized officer, Philippe Bécamel, *International Preliminary Report on Patentability*, Application No. PCT/US2013/025021, Dated Aug. 12, 2014, 7 pages.
(Continued)

*Primary Examiner* — Peter Macchiarolo
*Assistant Examiner* — Anthony W Megna Fuentes
(74) *Attorney, Agent, or Firm* — Sunstein Kann Murphy & Timbers LLP

(57) ABSTRACT

Disclosed are collection devices, kits, and methods for collecting and transporting one or more samples. A collection device of the present invention includes a central panel including a detachable sample strip. The sample strip has a sampling area for applying a sample on each side of the sample strip. The collection device includes two flaps, each capable of covering a portion of the sample strip that includes a sampling area. Consequently, a user is not exposed to a first sample when applying a second sample. Additionally, the sample strip can be detached without uncovering the sample strip.

28 Claims, 10 Drawing Sheets

(52) U.S. Cl.
    CPC ... *B01L 2200/185* (2013.01); *B01L 2300/0663* (2013.01); *B01L 2300/0809* (2013.01); *B01L 2300/0825* (2013.01); *B01L 2300/16* (2013.01)

(56) References Cited

U.S. PATENT DOCUMENTS

| | | | |
|---|---|---|---|
| 6,326,214 B1 | 12/2001 | Liu et al. | 436/518 |
| 7,587,793 B2* | 9/2009 | Sangha | 422/550 |
| 2004/0204661 A1* | 10/2004 | Epler | 600/572 |
| 2005/0196318 A1* | 9/2005 | Matusewicz et al. | 422/58 |
| 2005/0220677 A1 | 10/2005 | Sangha | 422/102 |
| 2006/0202008 A1* | 9/2006 | Purcell et al. | 229/301 |
| 2006/0282013 A1* | 12/2006 | Kauffmann et al. | 600/572 |
| 2009/0132204 A1* | 5/2009 | Bodlaender et al. | 702/188 |
| 2010/0047129 A1* | 2/2010 | LaStella et al. | 422/68.1 |

FOREIGN PATENT DOCUMENTS

| | | |
|---|---|---|
| WO | WO 90/03927 | 4/1990 |
| WO | WO 00/76664 A1 | 12/2000 |

OTHER PUBLICATIONS

European Patent Office, Authorized officer Ralph Tiede, *International Search Report*, Application No. PCT/US2013/025021, dated Jun. 6, 2013, 5 pages.

European Patent Office, Authorized officer Ralph Tiede, *International Search Report Written Opinion*, Application PCT/US2013/025021, dated Jun. 6, 2013, 6 pages.

\* cited by examiner

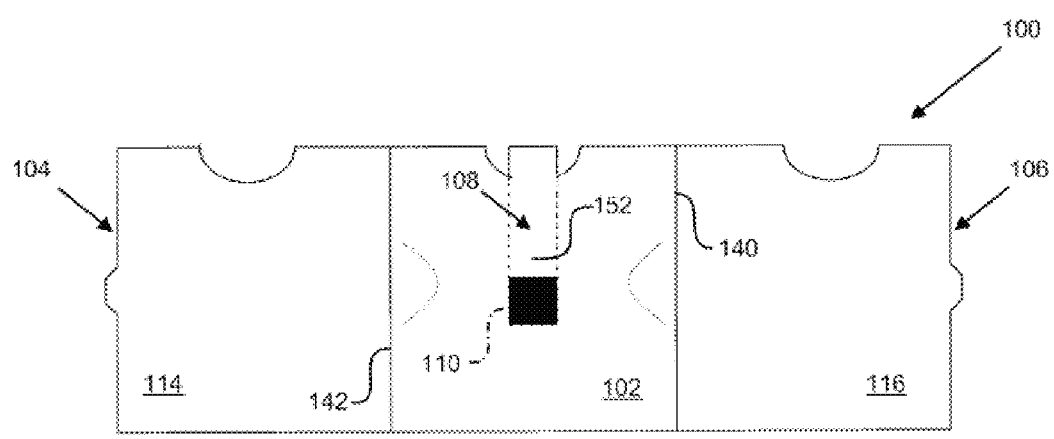
FIG. 1A
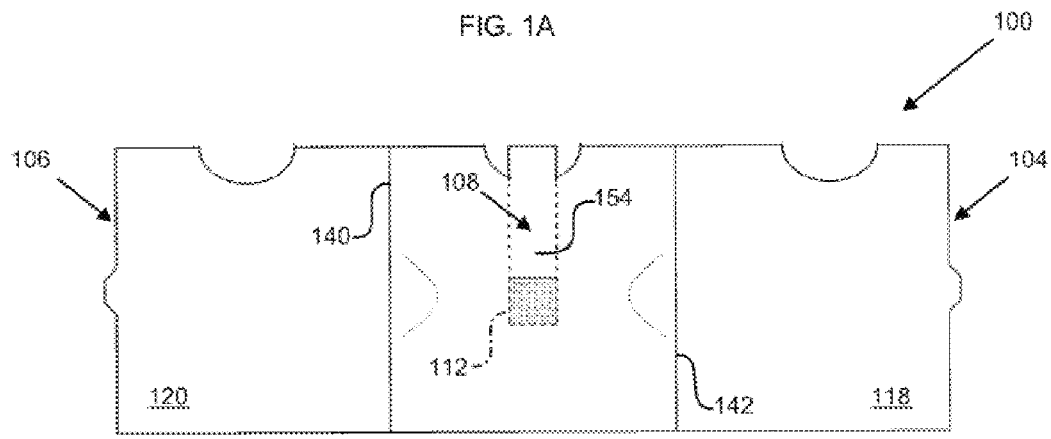
FIG. 1B
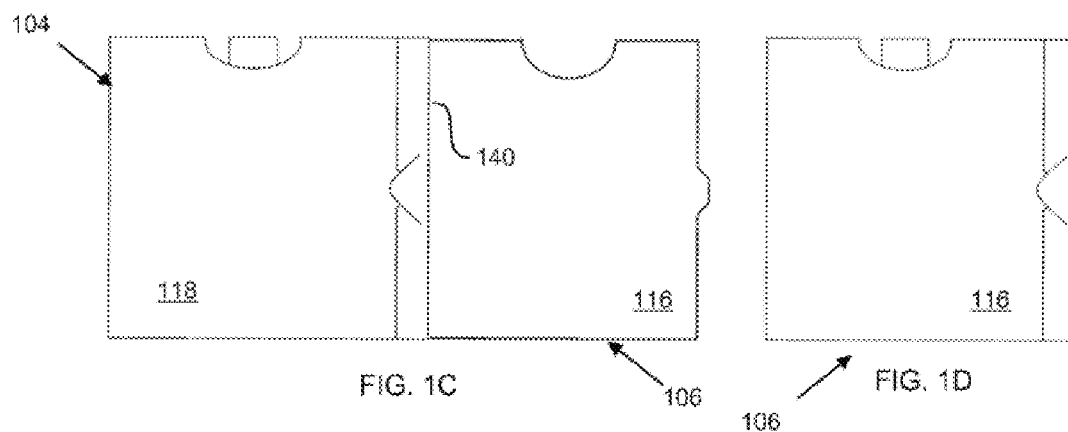
FIG. 1C
FIG. 1D

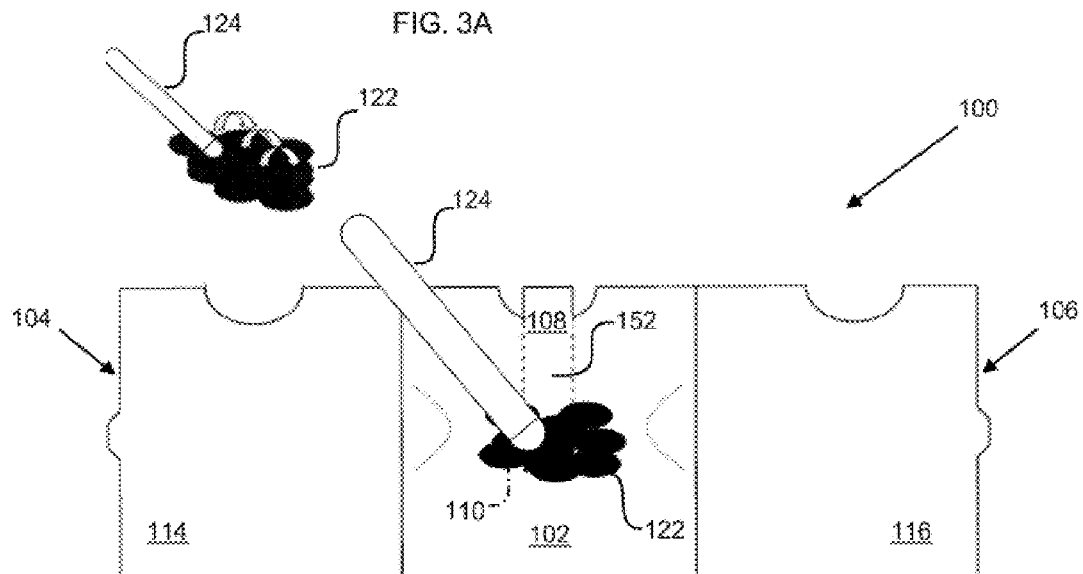
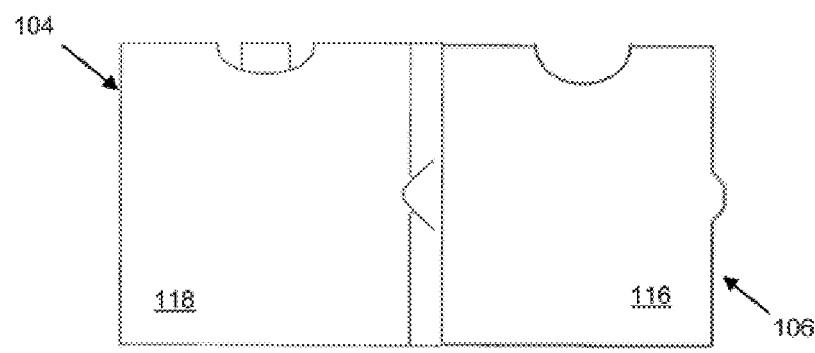
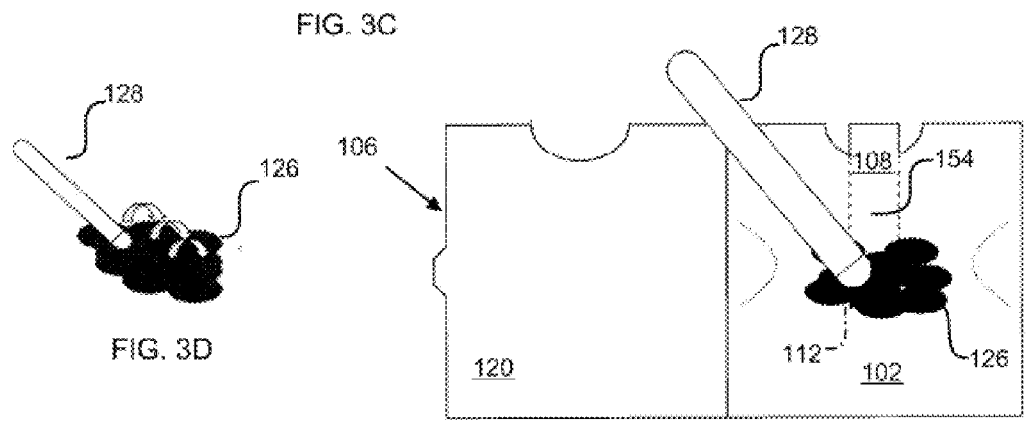

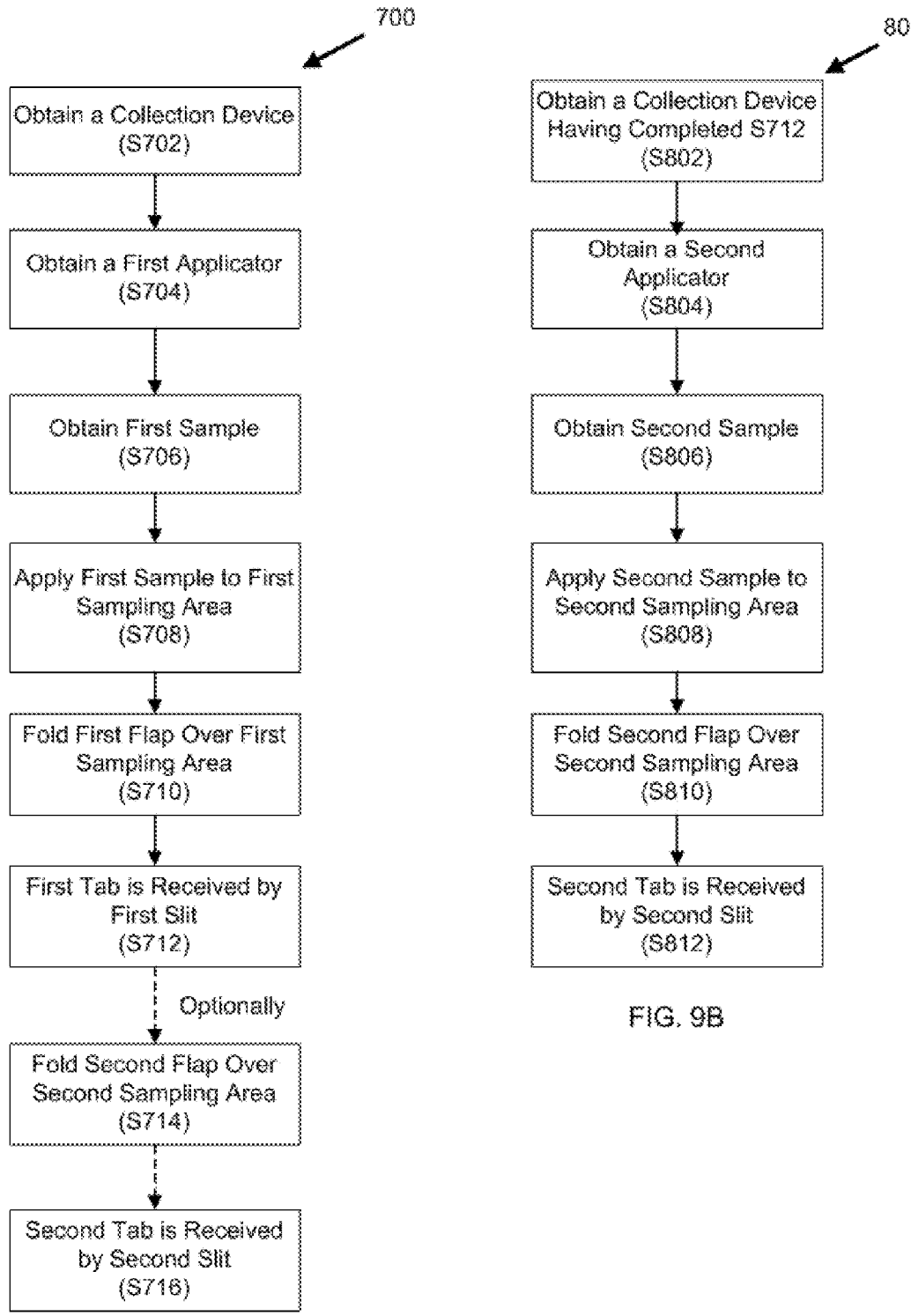

SAMPLE COLLECTION AND TRANSPORT DEVICES, METHODS, AND KITS

CROSS-REFERENCE TO RELATED APPLICATIONS

This application claims the benefit of U.S. Provisional Application No. 61/597,676, filed Feb. 10, 2012, the entire contents of which is incorporated herein by reference in its entirety.

BACKGROUND OF THE INVENTION

Collection cards are useful for holding and transporting a sample. Typically, collection cards capable of holding and transporting two or more samples include a plurality of sampling areas that face the same direction. Consequently, a user is exposed to a first sampling area that is holding a first sample when applying a second sample.

SUMMARY OF THE INVENTION

Devices, methods, and kits for collecting and transporting one or more samples are disclosed.

One aspect of the present invention provides a collection device for collecting one or more samples. The collection device includes a first flap, a second flap, and a central panel. The central panel includes a sample strip having a first side containing a first sampling area and a second side containing a second sampling area. The collection device is adapted and configured to receive a first sample on the first sampling area and a second sample on the second sampling area. The first sample on the first sampling area can be covered by the first flap when the second sample is received on the second sampling area.

This aspect of the invention can have a variety of embodiments.

The collection device can include a central panel having perforations that define at least a distal portion of the sample strip. Sampling areas are located on the distal portion of the sample strip. The sampling areas can be embossed.

The collection device can include a first foldable portion on a first border between the first flap and the central panel and a second foldable portion on a second border between the second flap and the central panel. The foldable portions each can be a structural feature. Examples of such structural features include a crease, a perforation, a score, or a printed mark. The first flap can be folded along the first foldable portion to cover the first sampling area and the second flap can be folded along the second foldable portion to cover the second sampling area. The proximal end of the sample strip can extend beyond a first proximal edge of the first flap and beyond a second proximal edge of the second flap.

The collection device can include a central panel having a first slit for receiving the first flap and a second slit for receiving the second flap. The first flap can include a first tab that is received by the first slit and the second flap can include a second tab that is received by the second slit.

The collection device can include a sample strip having a handle at its proximal portion. The handle can be formed by two or more cuts that separate the handle from the central panel. The proximal end of the handle can be wider than a distal end of the handle. The handle can extend beyond a proximal edge of the first flap and beyond a proximal edge of the second flap.

The collection device can be formed from cardboard.

The collection device can be formed from a single piece of cardboard.

The collection device can be made from a natural material or a synthetic material that can be formed into a solid planar shape. Examples include but are not limited to cloth and plastic.

The collection device can be substantially coated with a varnish. The collection device can include an area for writing. In some embodiments, the varnish does not coat the first sampling area, the second sampling area, or the area for writing.

The sample collected can be a biological sample including blood, cells, feces, milk, mucus, phlegm, pus, saliva, semen, sweat, tear, urine, vaginal secretions, or vomit.

The sample collected can be a non-biological sample. The type of non-biological sample is not limiting and can be an organic or inorganic sample as long as it can be reversibly attached to the collection device. Examples include but are not limited to chemical, dust, food, mineral, oil, sludge, soil, waste, and water.

Another aspect of the present invention is a method for collecting one or more samples. The method includes a first step of obtaining a collection device including any combination of the aforementioned embodiments of the above aspect. The second step is applying a first sample to the first sampling area. The third step is covering the first sample with the first flap. Optionally, the method can further include steps of applying a second sample to the second sampling area and covering the second sample with the second flap.

Another aspect of the present invention is a method for using a collection device. The method includes a first step of obtaining a collection device including any combination of the aforementioned embodiments of the above aspect. The second step is grasping a proximal portion of the sample strip. The third step is pulling the sample strip to separate the sample strip from the central panel. Optionally, the method can further include a step of contacting said sample strip with a solvent.

Another aspect of the present invention is a kit including a collection device including any combination of the aforementioned embodiments of the above aspect, a first applicator for applying a first sample, a second applicator for applying a second sample, a mailing envelope capable of holding the collection device, instructions for use, and a package capable of holding the device, the applicators, the mailing envelope, and the instructions.

Other features and advantages of the invention will be apparent from the detailed description and from the claims.

FIGURES

For a fuller understanding of the nature and desired objects of the present invention, reference is made to the following detailed description taken in conjunction with the figures wherein:

FIG. 1A depicts one embodiment of a collection device showing a first side of the sample strip and the device in an open configuration.

FIG. 1B depicts the collection device of FIG. 1A but showing a second side of the sample strip.

FIG. 1C depicts the collection device of FIG. 1A with a first flap covering the first side of the sample strip.

FIG. 1D depicts the collection device of 1C with a second flap covering the second side of the sample strip.

FIGS. 3A to 3E depict steps for collecting two samples using the collection device of FIG. 1A.

Figure 8A:
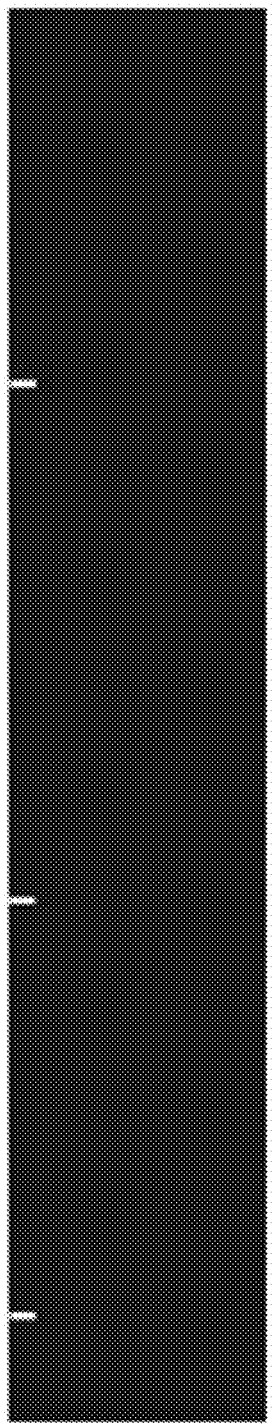
Figure 8B:
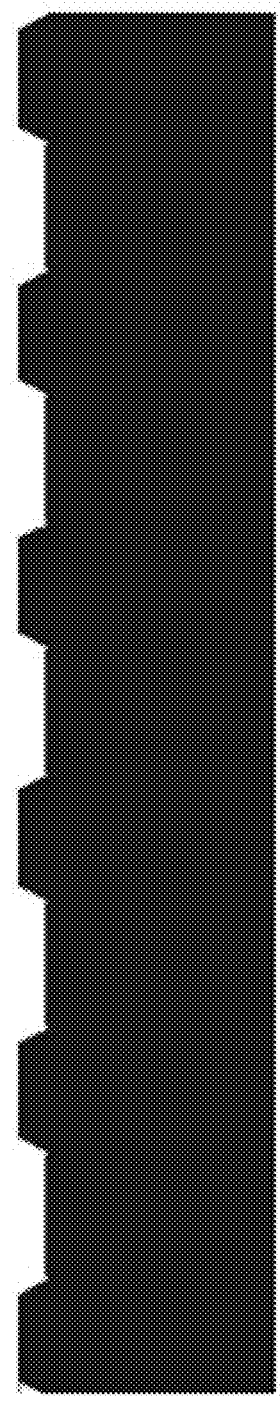

FIGS. 8A and 8B depict side views of cutting dies for making perforations. The die illustrated in FIG. 8A produces a "Nick" pattern of perforations. The die illustrated in FIG. 8B produces a "Skip Score" pattern of perforations.

FIGS. 9A and 9B depict methods for collecting one (FIG. 9A) or two (FIG. 9B) samples.

Figures 10A, 10B:
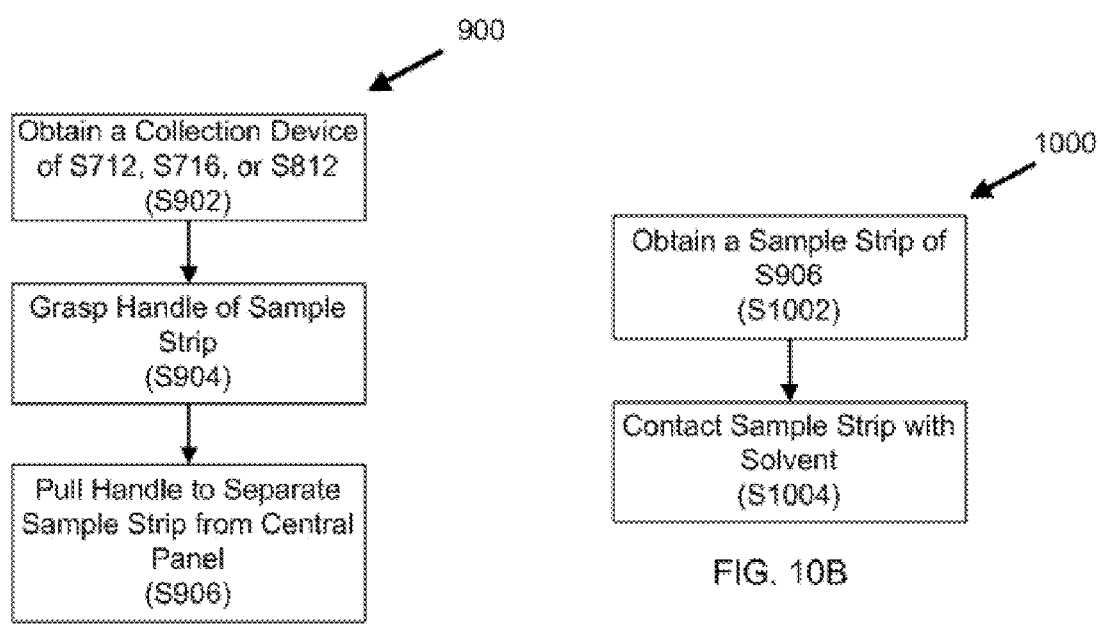

FIGS. 10A and 10B depict methods for using a sample strip comprising one or two samples.

DETAILED DESCRIPTION

The instant invention is most clearly understood with reference to the following definitions:

The term "patient", "subject", or "donor" shall be understood to refer to any organism from which a biological sample is desired. Applicants envision collecting biological samples from bacteria, fungi, plants, protozoa, and animals. Animals include non-mammals and mammals. Mammals, include, but are not limited to, a human or non-human mammal, such as a bovine, canine, equine, feline, ovine, primate, or rodent. A "user" is one who collects, obtains, or analyzes a sample. The "user" can be the "patient", "subject", or "donor" him/herself. The "user" can be a biologist, chemist, environmental scientist, geologist, health care professional, laboratory technician, physical scientist, veterinarian, or one who has received training in collecting, transporting, and analyzing a sample.

The term "sample" shall be understood to refer to a solid or liquid specimen that is capable of being collected and being reversibly attached to the collection device.

The term "biological sample" shall be understood to refer to a solid or liquid specimen from a multicellular organism. For microorganisms, the term, "biological sample" would apply to entire organisms that may be collected in mass. For animals, examples of a "biological sample" include blood, cells, feces, milk, mucus, phlegm, pus, saliva, semen, sweat, tear, urine, vaginal secretions, and vomit, if present in that animal.

The term "applying" shall be understood to refer to physically contacting a sample with a collection device such that the sample is reversibly attached to the collection device. Synonyms for "applying" include affixing, covering, dabbing, painting, placing, rubbing, smearing, spreading, and sticking. The term "applicator" shall be understood to refer to any item that is capable of obtaining a sample and applying it to a collection device. Non-limiting examples of an applicator include a cotton swab, a glove, a pipette, a probe, a spatula, a stick, a syringe, a tissue, and a tube.

The term "cardboard" shall be understood to refer to any type of a heavy-duty paper. Examples include card stock, cover stock, poster board, and pasteboard, as well as the generally-known types of cardboard. The thickness of the cardboard can vary from 8 point (pt) to 18 pt e.g., 8 pt, 9 pt, 9.5 pt, 10 pt, 10.5 pt, 11 pt, 12 pt, 13 pt, 14 pt, 15 pt, 16 pt, and 18 pt. An example of a preferred cardboard is 12 pt C2S.

The term "perforation" shall be understood to refer to a series of holes made into a material which allows easier separation of two sections of the material. The holes may be circular or may be elongated. The process of creating perforations is well known in the art, which involves puncturing the material with a tool. Creating perforations may be by a hole punch or a cutting edge that includes "nicks," i.e., indentations, where the two sections of the material are not separated. Alternately, they can be made by a cutting wheel or a grinding wheel that includes nicks in the wheel's circumference. Perforations may define a component of a collection device, for example, the shape and size of a sample strip may be defined by perforations made in the collection device's central panel.

The term "cut" shall be understood to refer to the physical separation by mechanical force of a feature of a collection device from another feature of the collection device. A "slit" may be formed by one or more cuts made in a central panel of the collection device. A "handle" of a sample strip may be formed from the central panel by one or more cuts. Additionally, a "cut" may physically separate the collection device from excess material from which the collection device is made but not included in the collection device. Separation of excess material may define features on the collection device. A cut may be formed with a die or wheel including a sharp edge.

The term "embossed" shall be understood to refer to a portion of a collection device having a surface that is raised, sunken, designed, textured, or in relief. An "embossed" portion can be made by applying physical pressure to one or both sides of the portion of the collection device. The pressure may be applied by fixed dies that squeeze, e.g., press, punch, or stamp, the material of the collection device or by roller dies through which the collection device is passed under pressure. An "embossed" portion of a collection device allows for better retention of a sample when compared to a non-embossed portion of the collection device.

The term "foldable portion" shall be understood to refer to a portion of a collection device that is capable of being folded. The "foldable portion" may be formed in advance to promote folding, i.e., by weakening a portion of the collection device. A "foldable portion" may include a crease, a groove, an indentation, a nick, a perforation, or a score. Methods of such treatments are well-known in the art. For example, the device can be "Skip Scored," using a piece of manufactured cutting rule that establishes a uniformed cutting pattern and weakens a material in one specific area. The "foldable portion" may be identified by a printed mark including a line, a dashed line, or a dotted line. The "foldable portion" may be identified by a printed arrow that points to it. Additionally, the "foldable portion" may be identified by text which specifies where a device can be folded. The "foldable portion" may not include a crease, a groove, an indentation, a nick, a perforation, or a score, as examples, yet is capable of being folded. In such a case, it is helpful for such a "foldable portion" to be identified by a printed mark.

The term "varnish" shall be understood to refer to a coating by a compound to impart certain desirable qualities to a cardboard including increased weight, strength, surface gloss, or smoothness, and also reduced moisture absorbency. Examples of a varnish useful for coating a cardboard are well known in the paper manufacturing arts. Non-limiting examples include a binder, calcium carbonate, chalk, china clay, dispersant, glue, kaolinite, latex, resin, starch, and styrene-butadiene. These may be used in any combination. Portions of the collection device that are not coated with a varnish have better retention of a sample or are better able to be written on with a pencil or an ink pen when compared to a varnished portion of the collection device.

The term "solvent" shall be understood to refer to a substance or force that is capable of removing a sample from a collection device. The solvent can be a liquid, which produces a solution comprising the sample and the solvent. The liquid solvent may be an aqueous, i.e., water-based, solvent. Such an aqueous solvent may contain electrolytes and non-electrolytes. Aqueous solvents are well known in the art. Non-limiting examples of aqueous solvents include HEPES-buffered saline (HBS), phosphate buffered saline (PBS), a saline-containing solution, TRIS-buffered saline (TBS), and water, as well as other buffering solutions commonly used in a biological, chemical, or medical laboratory. The liquid solvent can be a non-aqueous liquid, including a non-polar solvent, a polar aprotic solvent, or a polar protic (yet not water-based) solvent. Examples of such non-aqueous liquid solvents are well known in the art. The solvent may be a solid. An example of a solid solvent is a scraping device that physically removes a sample from the collection device. The solvent may be fire or high temperature which burns away the collection card and leaves the non-combustible components of a sample.

The term "side" shall be understood to refer to one of two opposite faces of a substantially planar structure/surface. In the present context, only one side of the substantially planar structure/surface (e.g., a sample strip) can be viewed by direct sight.

The term "can be" shall be understood to refer to an initial, an intermediate, or a final configuration of a device or feature of the device having a specified capability. For example, a feature that "can be folded" may be initially obtained in an unfolded configuration but later may be placed in a folded configuration.

In this disclosure, "comprises," "comprising," "containing" and "having" and the like can have the meaning ascribed to them in U.S. patent law and can mean "includes," "including," and the like. "Consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

As used herein, "obtaining" as in "obtaining a collection device" includes purchasing, receiving, or otherwise acquiring a device, item, or sample.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood to be within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any product, device, structural feature, or method provided herein can be combined with one or more other product, device, structural feature, or method provided herein.

DESCRIPTION OF THE INVENTION

Aspects of the present invention provide devices, methods, and kits for collecting and transporting one or more samples.

Sample Collection and Transport Devices

Referring to FIGS. 1A and 1B, opened configurations of collection device 100 are shown. Device 100 includes a first flap 104, a second flap 106, and a central panel 102. First flap 104 includes a first side 114 and a second side 118. Second flap 106 includes a first side 116 and a second side 120. Central panel 102 includes a sample strip 108 that is defined by perforations made into the central panel 102. Sample strip 108 includes a first side 152 and a second side 154. First side 152 includes sampling area 110 and second side 154 includes second sampling area 112. Collection device 100 includes foldable portions 140 and 142 that allow first flap 104 and second flap 106 (respectively) to cover a portion of central panel 102, i.e., the portions comprising sampling areas 110 and 112, respectively.

Referring to FIGS. 1C and 1D, a collection device 100 in two closed configurations is shown. In FIG. 1C, first flap 104 is folded over (i.e., covers) the first sampling area 110 of sample strip 108. In this configuration, side 114 of the first flap 104 is facing the first sampling area 110 and side 118 of the first flap 104 is outward facing. In FIG. 1D, the second flap 106 is folded over (i.e., covers) the second sampling area 112 of sample strip 108. In this configuration, side 120 of the second flap 106 faces the second sampling area 112 and side 116 of the second flap 106 faces outward.

Figure 2A:
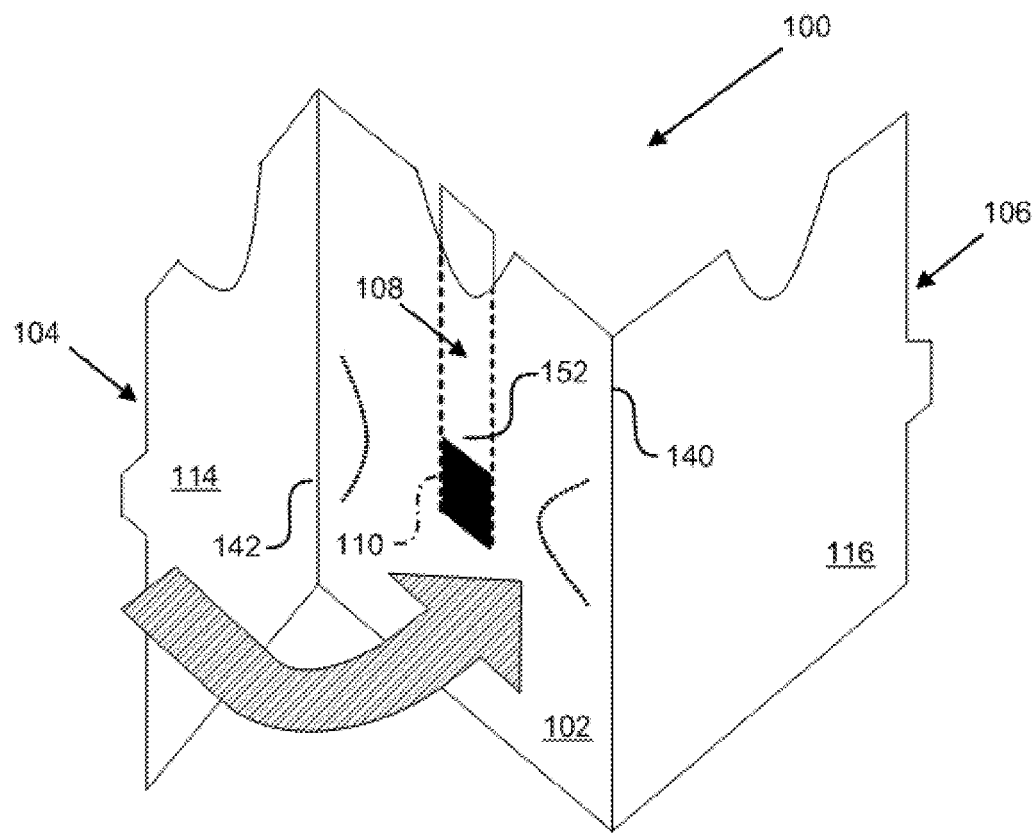
FIG. 2A depicts the collection device of FIG. 1A as the first flap is being folded along a first foldable portion to cover the first side of the sample strip.
Figure 2B:
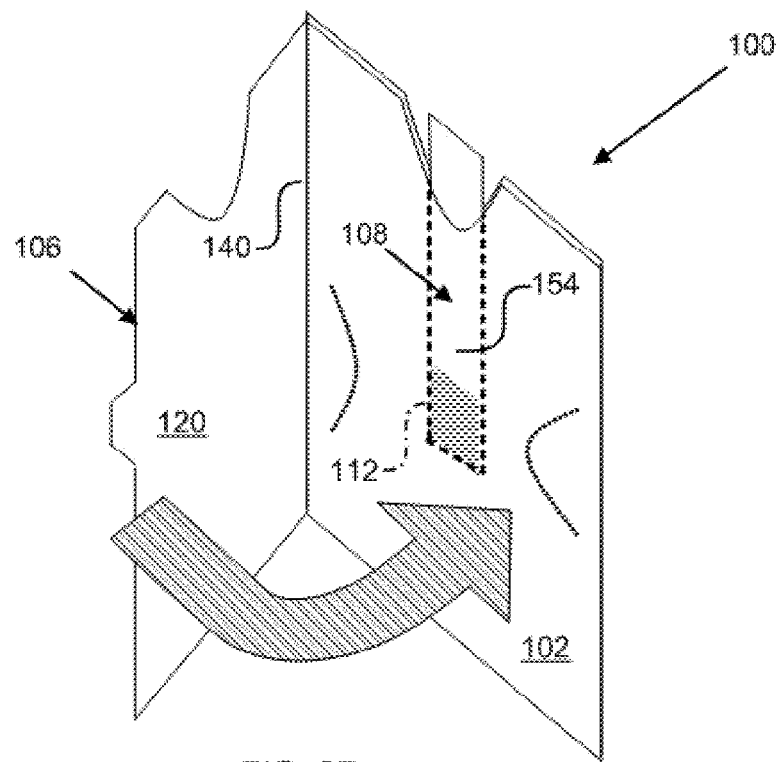
FIG. 2B depicts the collection device of FIG. 2A as the second flap is being folded along a second foldable portion to cover the second side of the sample strip.

Referring to FIGS. 2A and 2B, the collection device 100 of FIG. 1A is shown during the folding processes. In FIG. 2A, foldable portion 142 is being folded, thereby allowing first flap 104 to fold over (i.e., cover) first sampling area 110. In FIG. 2B, the device, after the folding process illustrated in FIG. 2A, is having its second foldable portion 140 folded, thereby allowing second flap 106 to fold over (i.e., cover) second sampling area 112.

The configurations of collection device 100 illustrated in FIGS. 1 and 2 are possible with the other embodiments of collection devices in the present invention. In other words, each of the various embodiments possesses equivalent structural features necessary to attain the configurations illustrated in FIGS. 1 and 2. For example, each embodiment of a collection device has a first foldable portion allowing a first flap to cover a first sampling area of a sampling strip.

Referring to FIG. 3A to 3E, a use of the collection device of FIGS. 1 and 2 for collecting two samples is shown. In FIG. 3A, a first applicator 124 obtains a first sample 122. Although applicator 124 appears to be a solid tubular structure, any suitable item can be used as an applicator in the present invention. Non-limiting examples of an applicator include a cotton swab, a glove, a pipette, a probe, a spatula, a stick, a syringe, a tissue, toilet paper, and a tube. In FIG. 3B, first applicator 124 applies a first sample 122 to a first sampling area 110 (on the first side 152) of sample strip 108. In FIG. 3C, first flap 104 is folded over (i.e., covers) the first sampling area 110 of sample strip 108, which contains the first sample 122. In FIG. 3D, a second applicator 128 obtains a second sample 126. In FIG. 3E, second applicator 128 applies a second sample 126 to a second sampling area 112 (on the second side 154) of sample strip 108. Next, the second flap 106 is folded over (i.e., covers) the second sampling area 112 of sample strip 108 (not shown).

Figure 4A:
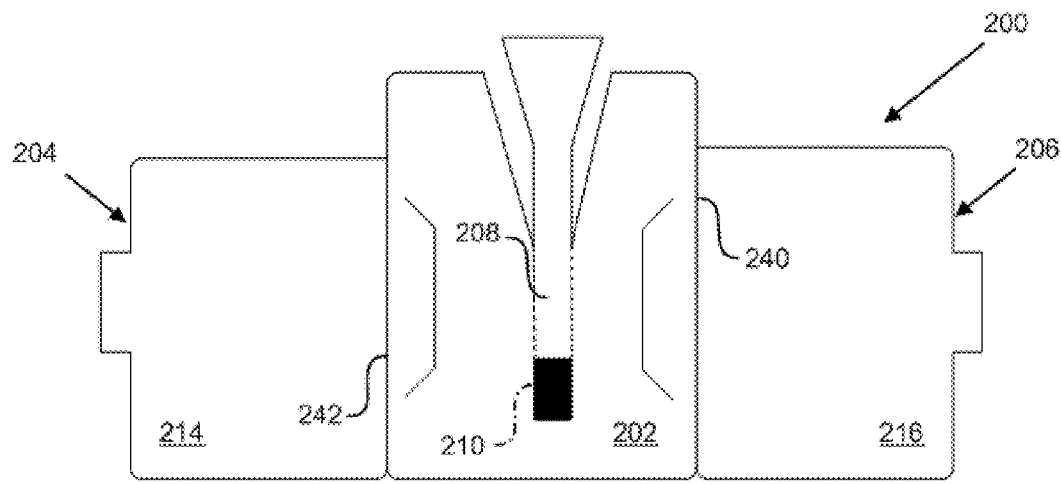
FIGS. 4A to 4C depict various embodiments of collection devices.
Figure 4B:
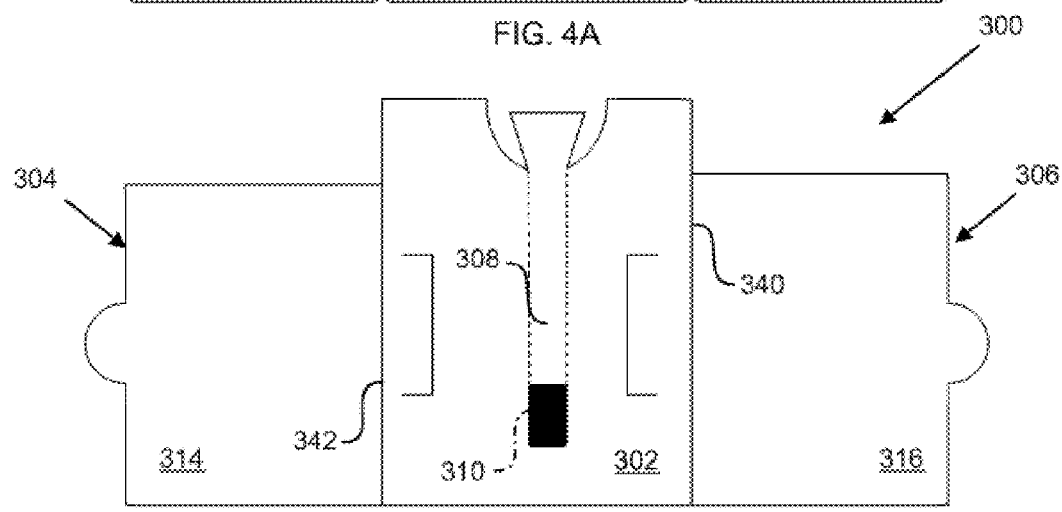
Figure 4C:
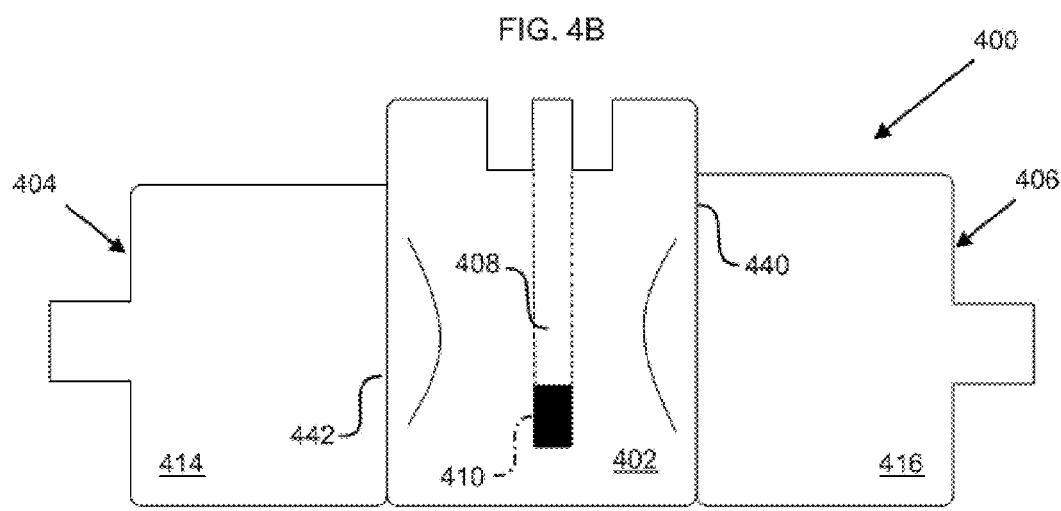

Referring to FIGS. 4A to 4C, opened configurations of collection devices 200, 300, and 400, with first sampling areas 210, 310, and 410 of sample strips 208, 308, and 408 (respectively) facing outward are shown. FIG. 4A shows a collection device 200 having a triangular-shaped handle, which extends beyond a proximal edge of a central panel, a triangular-shaped cut out from the central panel, rectangular tabs, trapezoidal slits, and rounded corners. FIG. 4B shows a collection device 300 having a triangular-shaped handle, which does not extend as far as a proximal edge of a central panel, a generally-circular-shaped cut out from the central panel, generally-circular-shaped tabs, rectangular slits, and squared corners. FIG. 4C shows a collection device 400 having a rectangular-shaped handle, which extends as far as a proximal edge of a central panel, a rectangular cut out from the central panel, square tabs, curved slits, and rounded corners. Each of collection devices 200, 300, and 400 includes equivalent structural features of collection device 100 illustrated in FIGS. 1A and 1B. Consequently, the configurations of collection device 100 illustrated in FIGS. 1 to 3 are possible with collection devices 200, 300, and 400.

Figure 5A:
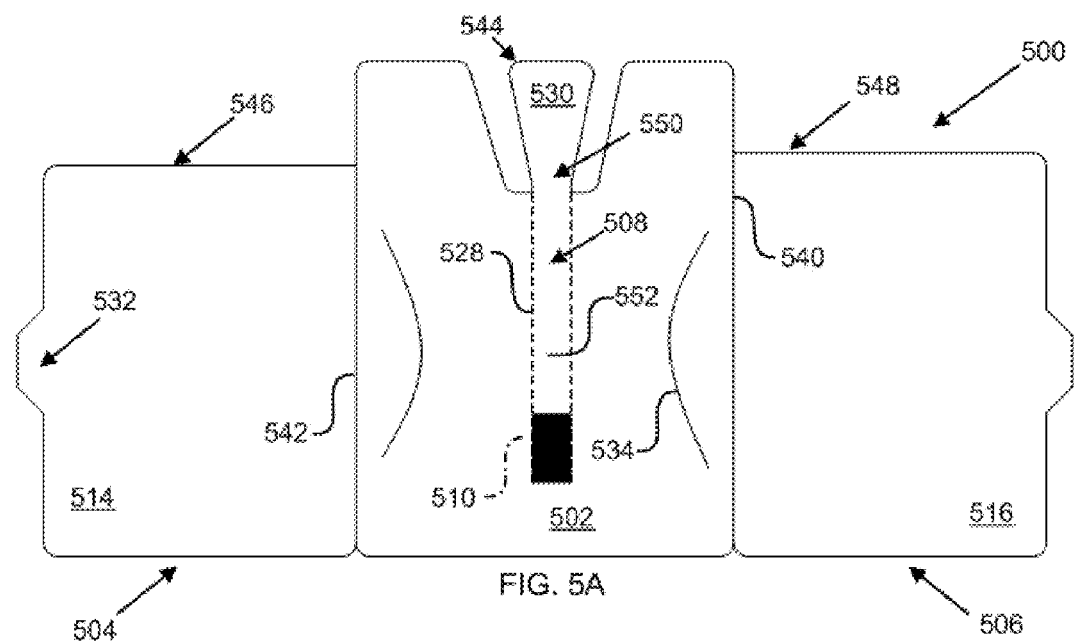
FIG. 5A depicts another embodiment of a collection device showing a first side of the sample strip, and with the device in an open configuration.
Figure 5B:
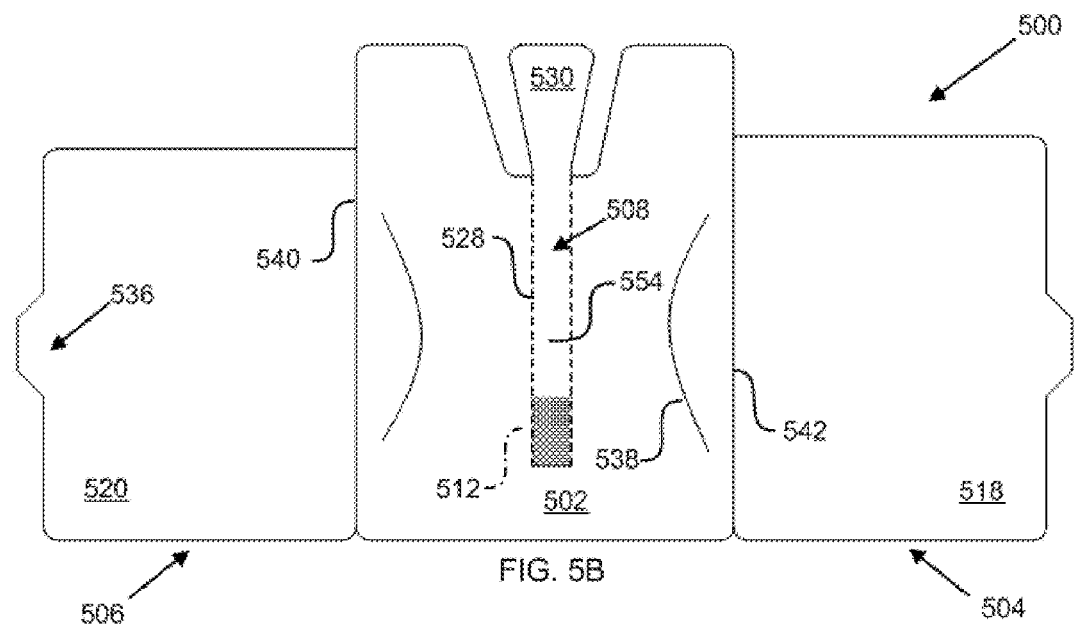
FIG. 5B depicts the collection device of FIG. 5A, but showing the second side of the sample strip, and with the device in an open configuration.

Referring to FIGS. 5A and 5B, opened configurations of collection device 500 is shown. FIG. 5A shows a first side of collection device 500, i.e., the side comprising a first sampling area 510. FIG. 5B shows a second side of collection device 500, i.e., the side comprising second sampling area 512. Collection device 500 includes a first flap 504, a second flap 506, and a central panel 502. First flap 504 includes a side 514 and a side 518. Second flap 506 includes a side 516 and a side 520.

Central panel 502 includes sample strip 508 that is defined by perforations 528 made into the central panel 502. The size, shape, and frequency of preferred perforations 528 varies depending on the material used for the collection card and how difficult it should be to separate sample strip 508 from central panel 502. For example, if a material is relatively stiff or thick, then larger (e.g., longer and wider) perforations and/or more frequent perforations may be required. Thus, less un-perforated material will connect sample strip 508 from central panel 502. Conversely, if it is desired that sample strip 508 be more tightly held onto a central panel 502, then smaller and/or less frequent perforations may be used. Examples of cutting dies for making perforations and skip scores are shown in FIGS. 8A and 8B, respectively.

Sample strip 508 includes a first sampling area 510 on a first side 552 of sample strip 508 and a second sampling area 512 on a second side 554 of sample strip 508. Having a first sampling area 510 on a first side 552 of sample strip 508 and a second sampling area 512 on a second side 554 of sample strip 508 allows a single sample strip 508 to contain two samples. These two samples are further processed (e.g., solubilized and analyzed) together. This allows a combined analysis of two samples that were collected at different times. Moreover, this allows a reduction of reagents necessary during further processing.

A handle 530 is positioned at the proximal end of sample strip 508. Handle 530 allows a user to more easily grasp (i.e., hold) sample strip 508, particularly when separating sample strip 508 from central panel 502. Handle 530 includes a proximal end 544 and a distal end 550. In the embodiment illustrated in FIGS. 5A and 5B, proximal end 544 is wider than distal end 550, thereby forming a generally triangular shaped handle 530. Some embodiments of the present invention have generally triangular shaped handles. A generally triangular shaped handle 530 provides more surface area to be grasped when separating sample strip 508 from central panel 502. Conversely, other embodiments of the present invention have handles in which a proximal end is not wider than a distal end. An example of which is collection device 100. Handle 530 is separated from central panel 502 by cuts. The cuts may be composed of straight lines or curves. Handle 530 may be separated but physically opposed to a central panel 502. Alternatively, material between handle 530 and central panel 502 may be removed to produce a square-shaped cut out, a generally-circular cut out, a triangular cut out, or trapezoidal cut out, as depicted in FIGS. 4A to 4C and 5A and 5B. A longer handle 530 (in the proximal-distal direction) is preferable to a shorter one since a longer handle 530 is less likely to break off when a sample strip 508 is separated from a central panel 502.

First flap 504 includes a first proximal edge 546. Second flap 506 includes a second proximal edge 548. As seen in FIGS. 5A and 5B, the proximal end 544 of handle 530 extends beyond proximal edges 546 and 548. In some embodiments, the handle does not extend beyond a proximal edge of a central panel (i.e., is flush with the edge or does not extend to the edge) as illustrated in FIGS. 4B to 4C. Having the proximal end 544 of handle 530 extending beyond proximal edges 546 and 548, allows a user to more easily grasp (i.e., hold) sample strip 508, particularly when separating sample strip 508 from central panel 502.

Collection device 500 includes two foldable portions 540 and 542. Foldable portions 540 and 542 are capable of being folded. Foldable portions 540 and 542 may include a crease, a groove, an indentation, a nick, a perforation, or a score. Foldable portions 540 and 542 may lack a crease, a grove, an indentation, a nick, a perforation, or a score. Foldable portions 540 and 542 may be identified by a printed mark including a line, a dashed line, or a dotted line. Foldable portions 540 and 542 may be identified by a printed arrow that points to the "foldable portion" or printed text which specifies where a device can be folded. Foldable portion 542 allows first flap 504 to cover the portion of central panel 502 which includes first sampling area 510. Foldable portion 540 allows second flap 506 to cover the portion of central panel 502 which includes second sampling area 512. In some embodiments, a foldable portion is defined only by printed markings.

Central panel 502 includes a first slit 534 and a second slit 538. These are formed by one or more cuts made into central panel 502. The shapes of first slit 534 and second slit 538 are non-limiting. For example, the slits may be a curve, a rectangular, a square, or a trapezoid as illustrated in FIGS. 4A to 4C. First flap 504 includes a first tab 532. Second flap 506 includes second tab 536. The shapes of first tab 532 and second tab 536 are non-limiting. For example, the tabs may be a curve, a rectangular, a square, or a trapezoid as illustrated in FIGS. 4A to 4C. First slit 534 is adapted and configured to receive first tab 532 and second slit 538 is adapted and configured to receive second tab 536.

When first flap 504 covers the portion of central panel 502 which includes first sampling area 510, first slit 534 is positioned to receive first tab 532; when first slit 534 is received by first tab 532, collection device 500 is in a reversible, yet stable first closed configuration. When in the first closed configuration, a first sample (not shown) applied to first sampling area 510 will not be exposed (i.e., to a user). This is advantageous in that first flap 504 protects the first sample from unfavorable environmental conditions, e.g., contaminants, dryness, moisture, and physical contact. Additionally, this is advantageous, as it prevents a user from exposure to the first sample, i.e., when applying a second sample. Importantly, no adhesive (e.g., glue or tape) is required to maintain the first closed configuration.

When second flap 506 covers the portion of central panel 502 that includes second sampling area 510, second slit 534 is positioned to receive second tab 532. When second slit 534 is received by second tab 532, collection device 500 is in a reversible, yet stable second closed configuration, i.e., a fully-closed configuration. This is advantageous in that second flap 506 protects the second sample from unfavorable environmental conditions, e.g., contaminants, dryness, moisture, and physical contact. Importantly, no adhesive (e.g., glue or tape) is required to maintain the second closed configuration.

First sampling area 510 and second sampling area 512 may be embossed, i.e., have a surface that is designed, in relief, raised, sunken, or textured. Methods of embossing are well known in the art. An embossed first sampling area 510 and second sampling area 512 each have better retention of a sample when compared to a non-embossed sampling area.

First sampling area 510 and second sampling area 512 may include an absorbent pad (not shown) that is adhered to the collection strip. The material and quantity of the absorbent pad could vary depending on the type of sample. For example, for generally liquid samples, an absorbent pad will have high liquid-absorbing qualities. Examples of absorbent pad include paper or cotton-based materials or absorbent resins. The absorbent pad may be held to sample strip 508 with an adhesive.

Collection devices of the present invention are made from a natural material or a synthetic material that can be formed into a solid planar shape. Examples include but are not limited to cloth, paper product, and plastic. An example of a paper product is cardboard. The term "cardboard" is defined above; generally, "cardboard" refers to any type of a heavy-duty paper. A collection device of the present invention may be cut from a single piece of cardboard. Alternately, the collection device could be formed from multiple pieces of cut cardboard, e.g., each comprising one of a central panel 502, a first flap 504, and a second flap 506, when using collection device 500 as an example. In this example, a junction is formed between central panel 502 and each of first flap 504 and second flap 506 with an adhesive (i.e., tape), thereby forming first foldable portion 540 and second foldable portion 542.

Edges can be substantially straight or not. Likewise, corners may be sharp (i.e., squared) or may be rounded.

A collection device can be substantially coated with a varnish. A varnish imparts certain qualities to a cardboard including weight, strength, surface gloss, smoothness, and reduced moisture absorbency. Varnish is not applied to first sampling area 510 and second sampling area 512. This allows for better retention of a sample when compared to a varnished area. Likewise, varnish is not applied to an area for writing. The area for writing is illustrated in FIG. 6A below.

Figure 7:
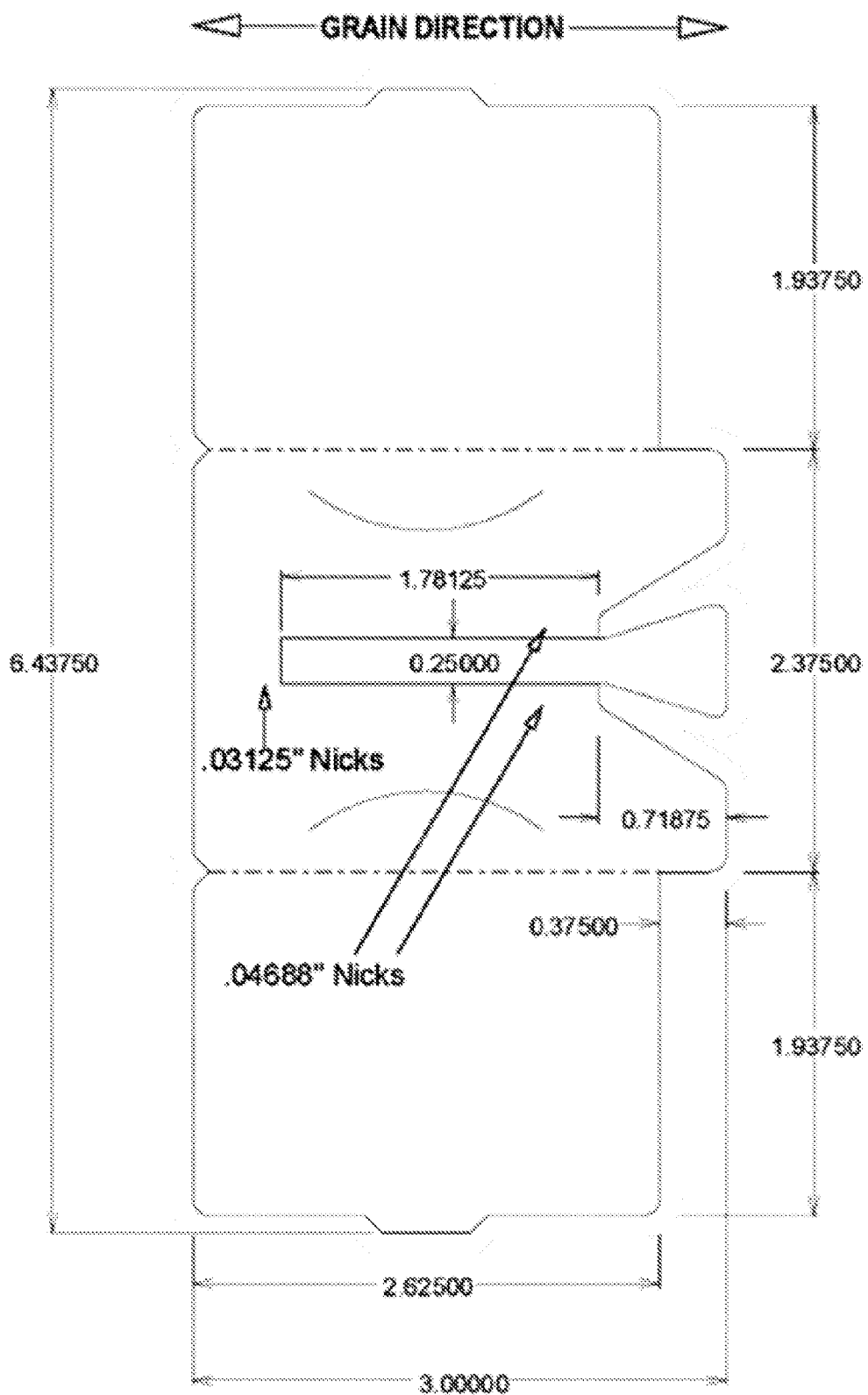
FIG. 7 depicts dimensions of an exemplary collection device.

The size and dimensions of a collection device is not limited. A long axis, as defined for collection device 500, is the distance between first tab 532 and second tab 536. A long axis can be between 3 and 8 inches. Preferable distances of a long axis are between 5 and 7 inches. Most preferably, the distance of a long axis is between 6 and 7 inches. A short axis, as defined for device 500, is the distance between proximal end 544 of handle 530 and the distal edge of central panel 502 (not shown). A short axis can be between 1 and 4 inches. Preferable distances of a short axis are between 1.5 and 4 inches. Most preferably, the distance of a short axis is between 2.5 and 3.5 inches. Dimensions of an exemplary collection device are depicted in FIG. 7.

Figure 6A:
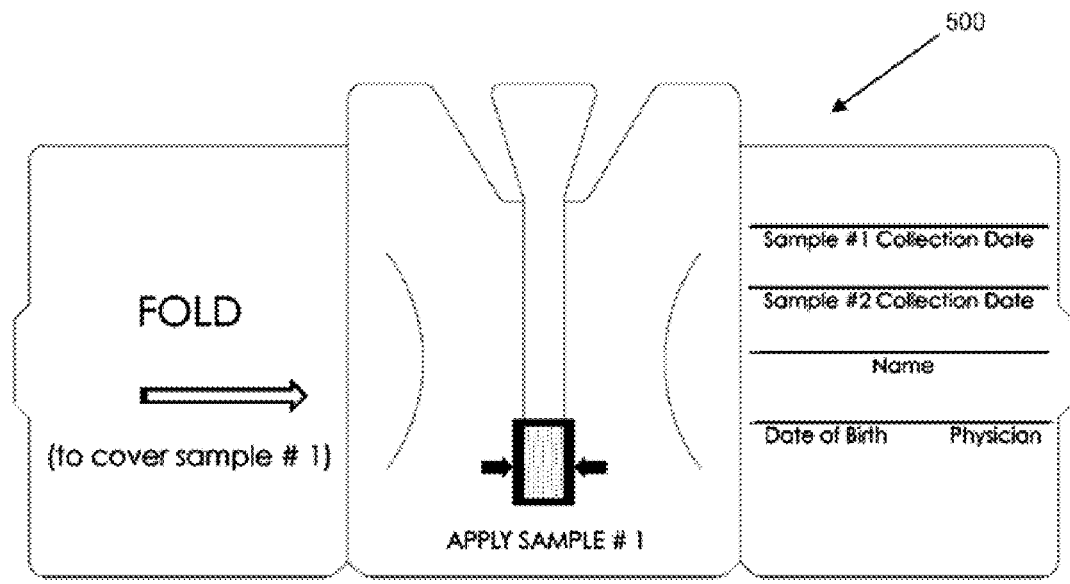
FIGS. 6A and 6B depict exemplary instructions and areas for writing printed on the device shown in FIGS. 5A and 5B.
Figure 6B:
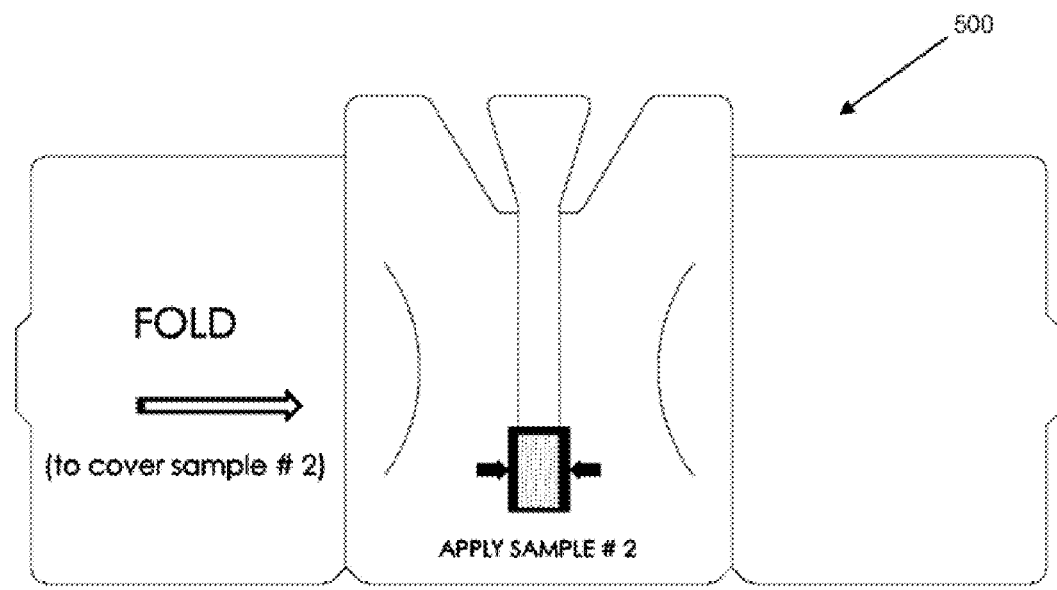

Referring to FIGS. 6A and 6B, exemplary instructions and areas for writing that can be printed on collection device 500 are shown. Collection device 500 includes a non-varnished writing area which allows a user to identify a donor of the sample, date of birth of the donor, a physician's name, and when a first and a second sample were collected. When a sample is collected from a non-human, the writing areas can be used to identify other features (e.g., species of organism and sample type). Likewise for non-biological samples, information identifying the sample can be included As seen in FIGS. 6A and 6B, the first and second sampling areas (not identified) are defined by a printed box and pointed to by printed arrows. This allows a user to know where a sample should be applied. It allows a user to know where to avoid applying the sample, i.e., on a portion of a sample strip not covered by a flap. The box also allows a user to know an estimate of the quantity of a sample that should be obtained.

The features described above for collection device 500 are included in each other embodiment of the present invention, i.e., collection devices 100 to 400 and collection devices considered but not shown in a drawing.

Methods for Collecting and Transporting One or More Samples

Referring now to FIGS. 9A and 9B, methods 700 and 800 for collecting one or more samples, respectively, are provided.

In step S702, an above-described collection device is obtained.

In step S704, an item suitable for collecting a sample is obtained, i.e., an applicator. Any item capable of obtaining a sample and applying it to the collection device is considered. The item may be purchased for the purpose of using with a collection device. Alternately, it could be a commonly used item from a household, laboratory, or medical office setting. A gloved human finger, following a rectal exam, would act as an applicator for obtaining a fecal sample.

In step S706, a first sample is obtained by the collection device of S702. The term sample is defined above. Samples can be non-biological or biological. Types of non-biological samples are not limiting. The sample must be able to be able to be applied and remain reversibly attached to a sampling area of a collection device. Examples of non-biological samples include but are not limited to chemical, dust, food, mineral, oil, sludge, soil, waste, and water. The term "biological sample" is defined above. Types of biological samples are not limiting. Examples of a "biological sample" include blood, cells, feces, milk, mucus, phlegm, pus, saliva, semen, sweat, tear, urine, vaginal secretions, and vomit.

The applicator is contacted with the sample in a manner and for as long as necessary to obtain a quantity of sample sufficient for subsequent analysis of the sample.

In step S708, the first sample of S706 is applied to the collection device of S702 using the applicator of S704. Applying simply means affixing, covering, dabbing, painting, placing, rubbing, smearing, spreading, and sticking. More specifically, the sample can be applied to a first sampling pad of a sample strip and the area surrounding the sampling area.

In step S710, a first flap of the collection device is articulated to cover the first sampling area containing the first sample. Using collection device 500 as an example, this step requires folding foldable portion 542 so that first flap 504 covers the portion of central panel 502 that contains the first sample.

Finally, in step S712, again using collection device 500 as an example, first tab 532 is received by first slot 534 to hold collection device 500 in a first closed configuration. At this point, the collection device is suitable for transport to a biologist, chemist, healthcare provider, laboratory technician, or physical scientist for analysis of the first sample.

Optionally, using collection device 500 as an example, in step S714, a second foldable portion 540 may be folded so that the second flap 506 covers a portion of central panel 502. In step S716, the second flap can be reversibly held in a second closed configuration when second tab 536 is received by second slit 538. The collection device is suitable for transport to a biologist, chemist, healthcare provider, laboratory technician, or physical scientist for analysis of the first sample.

Method 800 relates to applying a second sample to a collection device having completed step S712 or S716.

In step S802, the collection device of S712 or S716 is obtained.

In step S804, a second applicator is obtained. The second applicator is used to obtain a second sample in step S806. In step S808, the second sample of step S806 is applied to a second sampling area.

In step S810, a second flap of the collection device is articulated to cover the second sampling area containing the second sample. Using collection device 500 as an example, this step requires folding foldable portion 540 so that first flap 506 covers the portion of central panel 502 that contains the second sample.

Finally, in step S812, using collection device 500 as an example, the second flap 506 can be reversibly held in a second closed configuration when second tab 536 is received by second slit 538.

At this point, the collection device is suitable for transport to a user, for example, biologist, chemist, healthcare provider, laboratory technician, or physical scientist, for analysis of the first and second samples.

Method for Separating a Sample Strip from a Central Panel of a Collection Device Referring now to FIG. 10A, method 900 for separating a sample strip from a central panel of a collection device is provided.

In step S902, a collection device of step S712, S716, or S812 is obtained.

In step S904, a proximal portions (i.e., handle) of a sample strip is grasped. Grasping may be by fingers or a tool (e.g., forceps). A sufficient amount of force to securely hold the sample strip is used.

In step S906, the handle of the sample strip is pulled in a direction parallel to the foldable portions. It is unnecessary and not preferable to open a collection device from a first closed configuration or second closed configuration. By leaving the device in a closed configuration, it is less likely that a sample applied to a sampling area will become aerosolized when separating a sample strip from a central panel. This reduces risk of infection to a user that is performing this step. Since a sample strip is defined by perforations, it is unnecessary to use a mechanical device (e.g., scissors) to cut the sample strip away from the central panel. By not touching a mechanical device to the sampling area containing a sample, there is less risk of contamination (e.g., cross contamination from the mechanical device) and no need to sterilize the mechanical device between samples.

Method for Separating a Sample from a Sample Strip

Referring now to FIG. 10B, a method 1000 for separating a sample from a sample strip is provided.

In step S1002, a sample strip containing a sample of step S906 is obtained.

In step S1004, a sample is separated from a sampling area by contacting the sample with a solvent. The term "solvent" is defined above.

The solvent can be a liquid, which produce a solution comprising the sample and the solvent. The liquid solvent may be an aqueous, i.e., water-based, solvent. The liquid solvent can be a non-aqueous liquid, including a non-polar solvent, a polar aprotic solvent, or a polar protic (yet not water-based) solvent. The solvent may be a solid. The solvent may be fire or high temperature.

When the solvent is a liquid, it is capable of removing the sample from a collection device to produce a solution comprising the sample and the solvent. Solvents useful for this are well-known in the art. Non-limiting examples of aqueous solvents include HEPES-buffered saline (HBS), phosphate buffered saline (PBS), a saline-containing solution, TRIS-buffered saline (TBS), and water, as well as other buffering solutions commonly used in a biological/chemical laboratory. In relation to a liquid solvent, contacting may mean immersing, soaking, spraying, washing, and the like.

The solution comprising the sample and the solvent may be suitable for further analysis. The solution may require further steps before it is ready for further analysis.

A Kit for Collecting and Transporting a Sample

A collection device having any of the aforementioned embodiments can be included in a kit.

A kit will include a device, an envelop for transporting (i.e., mailing) to a laboratory or medical office a device containing a sample, instructions for use, and a package for holding at least each of the previously-mentioned items. The envelop shall meet standards set by the US Postal Service for mailing samples. Alternately, the kit can include a reversibly sealable plastic bag (i.e., zip-locking) that can hold a device after a first sample has been received. The kit may optionally contain a plurality of applicators for applying samples. The type of applicator may vary depending on the sample to be collected. For example, if a urine sample is to be collected, then a bulb-type pipette or syringe may be included in the kit; if a fecal sample is to be collected, then a stick or tissue may be included in the kit. Additional items may be included in the kit depending on the sample to be collected. For example, if a sample is blood, then the kit may contain a lancet for piercing the skin for obtaining a drop of blood. A kit may include a plurality of devices. Instructions will be included to help a user properly use the device. The type of package is not limiting; it can be a bag, box, pouch, or tube.

Equivalents

The functions of several elements may, in alternative embodiments, be carried out by fewer elements, or a single element. Similarly, in some embodiments, any functional element may perform fewer, or different, operations than those described with respect to the illustrated embodiment.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

We claim:

1. A collection device for collecting one or more samples comprising:
   a first flap; a second flap; and a central panel;
   wherein said central panel comprises a sample strip having a first side comprising a first sampling area and a second side comprising a second sampling area; wherein said first side is on the first of two opposite faces of a substantially planar surface, and wherein said second side is on the second of said two opposite faces of said substantially planar surface; wherein said collection device is adapted and configured to receive a first sample on said first sampling area and a second sample on said second sampling area;
   and wherein said first sample on said first sampling area can be covered by said first flap when said second sample is received on said second sampling area.

2. The collection device of claim 1, wherein said central panel comprises perforations that define at least a distal portion of said sample strip.

3. The collection device of claim 2, wherein said first sampling area and said second sampling area are located on said distal portion of said sample strip.

4. The collection device of claim 3, wherein said first sampling area and said second sampling area are embossed.

5. The collection device of claim 3, wherein said collection device comprises a first foldable portion on a first border between said first flap and said central panel and a second foldable portion on a second border between said second flap and said central panel; and wherein said first foldable portion and said second foldable portion each comprise a structural feature selected from the group consisting of a crease, a perforation, a score, and a printed mark.

6. The collection device of claim 5, wherein said first flap can be folded along said first foldable portion to cover said first sampling area and said second flap can be folded along said second foldable portion to cover said second sampling area.

7. The collection device of claim 6, wherein a proximal end of said sample strip extends beyond a first proximal edge of said first flap and beyond a second proximal edge of said second flap.

8. The collection device of claim 1, wherein said central panel comprises a first slit for receiving said first flap and a second slit for receiving said second flap.

9. The collection device of claim 8, wherein said first flap comprises a first tab that is received by said first slit and said second flap comprise a second tab that is received by said second slit.

10. The collection device of claim 2, wherein said sample strip comprises a handle at a proximal portion of said sample strip.

11. The collection device of claim 10, wherein said handle is formed by two or more cuts that separate said handle from said central panel.

12. The collection device of claim 11, wherein a proximal end of said handle is wider than a distal end of said handle; and wherein said proximal end of said handle extends beyond a first proximal edge of said first flap and beyond a second proximal edge of said second flap.

13. The collection device of claim 1, wherein said collection device is formed from cardboard.

14. The collection device of claim 1, wherein said collection device is formed from a single piece of cardboard.

15. The collection device of claim 3, wherein said collection device is substantially coated with a varnish.

16. The collection device of claim 15, wherein said collection device comprises an area for writing and wherein said varnish does not coat said first sampling area, said second sampling area, or said area for writing.

17. The collection device of claim 1, wherein each of said first sample and said second sample is a biological sample.

18. The collection device of claim 17, wherein said biological sample is selected from the group consisting of blood, cells, feces, milk, mucus, phlegm, pus, saliva, semen, sweat, tear, urine, vaginal secretions, and vomit.

19. A method for collecting one or more samples comprising:
obtaining a collection device comprising a first flap, a second flap, and a central panel, wherein said central panel comprises a sample strip having a first side comprising a first sampling area and a second side comprising a second sampling area, wherein said first side is on the first of two opposite faces of a substantially planar surface, and wherein said second side is on the second of said two opposite faces of said substantially planar surface, wherein said collection device is adapted and configured to receive a first sample on said first sampling area and a second sample on said second sampling area, and wherein said first sample on said first sampling area can be covered by said first flap when said second sample is received on said second sampling area; applying a first sample to said first sampling area; covering said first sample with said first flap.

20. The method of claim 19, further comprising: applying a second sample to said second sampling area; and covering said second sample with said second flap.

21. The method of claim 19, wherein each of said first sample and said second sample is a biological sample; wherein said biological sample is selected from the group consisting of blood, cells, feces, milk, mucus, phlegm, pus, saliva, semen, sweat, tear, urine, vaginal secretions, and vomit.

22. A method comprising the steps of obtaining a collection device comprising a first flap, a second flap, and a central panel, wherein said central panel comprises a sample strip having a first side comprising a first sampling area and a second side comprising a second sampling area, wherein said collection device is adapted and configured to receive a first sample on said first sampling area and a second sample on said second sampling area, wherein said first side is on the first of two opposite faces of a substantially planar surface, and wherein said second side is on the second of said two opposite faces of said substantially planar surface, wherein said first sample on said first sampling area can be covered by said first flap when said second sample is received on said second sampling area, wherein said sample strip contains at least a first sample on said first sampling area, and wherein said first flap covers said first sample on said first sampling area; grasping a proximal portion of said sample strip; and pulling said sample strip to separate said sample strip from said central panel.

23. The method of claim 22, further comprising a step of contacting said sample strip with a solvent.

24. The method of claim 22, wherein each of said first sample and said second sample is a biological sample.

25. A kit comprising: the collection device of claim 1, comprising a first flap, a second flap, and a central panel, wherein said central panel comprises a sample strip having a first side comprising a first sampling area and a second side comprising a second sampling area, wherein said collection device is adapted and configured to receive a first sample on said first sampling area and a second sample on said second sampling area, wherein said first side is on the first of two opposite faces of a substantially planar surface, and wherein said second side is on the second of said two opposite faces of said substantially planar surface and wherein said first sample on said first sampling area can be covered by said first flap when said second sample is received on said second sampling area; a mailing envelope capable of containing said collection device; instructions for use; and a package capable of containing said device, said mailing envelope, and said instructions for use.

26. The kit of claim 25, wherein said kit further comprises a first applicator for applying said first sample to said first sampling area and a second applicator for applying said second sample to said second sampling area.

27. The kit of claim 25, wherein each of said first sample and said second sample is a biological sample.

28. The kit of claim 26, wherein each of said first applicator and said second applicator is a tissue.

* * * * *